(12) United States Patent
Golio

(10) Patent No.: US 8,247,006 B2
(45) Date of Patent: Aug. 21, 2012

(54) COMPOSITION AND METHOD OF TREATING LIPID ENCAPSULATED VIRUS INFECTIONS

(76) Inventor: Dominick I. Golio, New York, NY (US)

( * ) Notice: Subject to any disclaimer, the term of this patent is extended or adjusted under 35 U.S.C. 154(b) by 0 days.

(21) Appl. No.: 12/820,862

(22) Filed: Jun. 22, 2010

(65) Prior Publication Data

US 2011/0311659 A1 Dec. 22, 2011

(51) Int. Cl.
*A61K 36/28* (2006.01)

(52) U.S. Cl. .......................... 424/737; 514/731; 562/562

(58) Field of Classification Search .................. None
See application file for complete search history.

(56) References Cited

U.S. PATENT DOCUMENTS

| | | | | |
|---|---|---|---|---|
| 4,424,232 A * | 1/1984 | Parkinson | ...................... | 514/468 |
| 5,215,748 A * | 6/1993 | Mankovitz | ..................... | 424/725 |
| 6,284,289 B1 * | 9/2001 | Van den Berghe | ............ | 424/746 |
| 6,362,225 B1 * | 3/2002 | Andreakos | ..................... | 514/561 |
| 2002/0009508 A1 | 1/2002 | Santhanam | | |
| 2002/0022052 A1 | 2/2002 | Dransfield | | |
| 2004/0081681 A1 | 4/2004 | Vromen | | |
| 2007/0292560 A1 | 12/2007 | Quan et al. | | |

OTHER PUBLICATIONS

Griffiths (Rev. Med. Virol. (2006), vol. 16, pp. 135-138).*
Coohill (Abstracts of the Annual Meeting of the American Society for Microbiology, (1983) vol. 83, pp. S41).*
Vimalanathan (Pharmaceutical Biology (2005), vol. 43, No. 9, pp. 740-745).*
International Search Report, dated Feb. 23, 2012, received in international patent application PCT/US2011/041390.
Written Opinion, dated Feb. 23, 2012, received in international patent application PCT/US2011/041380.

* cited by examiner

*Primary Examiner* — Susan Hoffman
(74) *Attorney, Agent, or Firm* — Daniels Patent Law PLLC; Scott A. Daniels

(57) ABSTRACT

A method of treating a patient infected with a lipid encapsulated virus by administering to the patient about 1000 mg to about 5000 mg per day of a nutritional supplement having from about 40 to about 80 wt. % L-lysine, from about 20 to about 50 wt. % butylated hydroxytoluene and from about 1 to about 10 wt. % *Echinacea*. Administration of the nutritional supplement inhibits ulcer formation resulting from lipid encapsulated virus infections such as herpes simplex I and II infections.

9 Claims, No Drawings

COMPOSITION AND METHOD OF TREATING LIPID ENCAPSULATED VIRUS INFECTIONS

FIELD OF THE INVENTION

The present invention relates to nutritional supplement compositions and their use in treating lipid encapsulated virus infections. In particular, the present invention relates to nutritional supplements including a combination of L-lysine, butylated hydroxy toluene (BHT) and *Echinacea*, and to the use of such nutritional supplements for the treatment of patients suffering from herpes simplex type I and II infections.

BACKGROUND OF THE INVENTION

Herpes simplex type I and type II viruses are two examples of the class of infective viruses known as lipid encapsulated viruses. This class of viruses includes a lipid envelope surrounding the protein coat (capsid) which protects the genetic material of the virus. Most lipid encapsulated viruses are dependent on the lipid envelope for the infectivity, as the lipid envelope facilitates penetration of host cell membranes. In addition to the above-identified herpes simplex type I and II viruses, examples of lipid encapsulated proteins include herpes zoster, cytomegalovirus, HIV, pseudorabies, west nile virus, hepatitis B and C, SARS and some strains of influenza, including avian flu. Accordingly, it is known to administer to infected patients substances which disrupt or interfere with virus lipid envelopes. There has not been demonstrated, however, a treatment effective in eliminating the virus completely from the host.

SUMMARY OF THE INVENTION

Wherefore, it is an object of the present invention to provide a nutritional supplement composition and method of treatment effective in treating lipid encapsulated virus infections.

Another object of the invention is to provide a nutritional supplement composition which prevents the formation of ulcers associated with lipid encapsulated virus infections such as those associated with the herpes simplex type I and II viruses.

A further object of the present invention is to provide a nutritional supplement composition which supports the immune system to bolster the host's ability to fight the infection.

Still another object of the invention is to provide a method for treatment and prophylaxis of lipid encapsulated virus infections.

These and other features, advantages and improvements according to this invention will be better understood by reference to the following detailed description.

DETAILED DESCRIPTION OF THE INVENTION

The present invention is directed to a method of treating a patient infected with a lipid encapsulated virus comprising administering to the patient an effective amount of a nutritional supplement including a combination of L-lysine, butylated hydroxytoluene and *Echinacea* as active ingredients.

The term "pharmaceutically acceptable carrier" as used herein means a non-toxic, generally inert vehicle for the active ingredients, which does not adversely affect the active ingredients, and which are suitable for ingestion by animals, including humans, without undue toxicity, incompatibility, instability, irritation, allergic response, and the like, commensurate with a reasonable benefit/risk ratio.

The term "effective amount" as used herein refers to an amount of the nutritional supplement sufficient to alleviate or reduce the symptoms of herpes simplex types I and II infections, other lipid enveloped virus infections and cold sores in the subject patient relative to the patient's symptoms prior to administration of the nutritional supplement. It is understood that the effective amount for any particular patient or subject depends upon a variety of factors including the age, body weight, general health, sex, diet, time of administration, route of administration, and rate of excretion, and the severity of the particular condition undergoing treatment.

The term "synergistic effect" when used in relation to the antiherpetic activity of the above defined combination means an antiviral or antiherpetic effect which is greater than the predictive additive effect of the individual components of the combination.

L-lysine is an essential amino acid having the chemical formula $HO_2CCH(NH_2)(CH_2)_4NH_2$ and the following chemical structure.

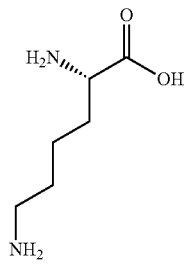

As an essential amino acid, lysine is not synthesized in animals, and must be ingested, either as lysine or as part of a lysine-containing protein. The nutritional requirement for humans is generally about 1.0 to about 1.5 g/day. Racemic lysine can be produced synthetically, but only the L-form is utilized in protein formation. The present invention can use either racemic or L-lysine, with the L-lysine form preferred.

Butylated hydroxytoluene (BHT, IUPAC: 2,6-di-tert-butyl-4-methylphenol) is a fat-soluble (lipophilic) organic compound commonly used as an antioxidant food additive. BHT has the molecular formula $C_{15}H_{24}O$ and the structure shown below.

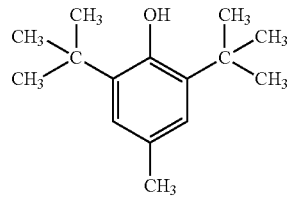

Butylated hydroxytoluene is metabolized in the liver and has a demonstrated low toxicity, and has been approved by the FDA for food, oils and fats. Due to its lipophilic structure, BHT is expected to disrupt the lipid envelope of lipid encapsulated proteins, rendering the virus more vulnerable to the host immune system and impairing the ability of the virus to penetrate through cell membranes into the host cells.

*Echinacea* is a genus of herbaceous plants in the family Asteraceae, informally referred to as purple coneflowers.

Species of *Echinacea* include at least: *Echinacea angustifolia*—Narrow-leaf Coneflower; *Echinacea atrorubens*—Topeka Purple Coneflower; *Echinacea laevigata*—Smooth Coneflower, Smooth Purple Coneflower; *Echinacea pallida*—Pale Purple Coneflower; *Echinacea paradoxa*—Yellow Coneflower, Bush's Purple Coneflower; *Echinacea purpurea*—Purple Coneflower, Eastern Purple Coneflower; *Echinacea sanguinea*—Sanguine purple Coneflower; *Echinacea simulata*—Wavyleaf Purple Coneflower; *Echinacea tennesseensis*—Tennessee Coneflower.

The present invention relates to a nutritional supplement composition for treating patients suffering from herpes simplex type I and II infections as well as other lipid enveloped viruses. The composition comprises a mixture of L-lysine, butylated hydroxy toluene and *Echinacea*, optionally with one or more pharmaceutically acceptable carriers. Preferably, the composition contains from about 40 to about 80 wt. % L-lysine, from about 20 to about 50 wt. % butylated hydroxytoluene and from about 1 to about 10 wt. % *Echinacea*, and particularly preferably from about 50 to about 70 wt. % L-lysine, from about 25 to about 40 wt. % butylated hydroxytoluene and from about 1 to about 10 wt. % *Echinacea*.

The composition can be administered by any standard means, for example, orally, topically and parentally, with oral administration preferred, for example, in the form of tablets, capsules, powders, granules or drops or in any other form which can be administered orally. The nutritional supplement may be ingested directly in a dry powder form or in admixture with solid or liquid food or beverages. When formulated in single dose forms such as tablets and capsules, the single dosage can include from about 5 to about 5000 mg of the combined active ingredients, preferably from about 1000 to about 3000 mg.

When utilizing the combination of active ingredients of this invention for treating viral infections, the composition is administered to a mammal in need of such treatment, e.g., humans, in a vehicle comprising one or more pharmaceutically acceptable carriers, the proportion of which is determined by the solubility and chemical nature of the composition components, chosen route of administration, standard biological practice, and the relative amounts of the active ingredients to provide a synergistic antiviral effect.

The composition of the present invention is effective to promote healing of ulcers resulting from lipid enveloped viruses such as herpes simplex type I and II.

The composition of the present invention also has utility in preventing formation of ulcers resulting from such lipid enveloped viruses. Nascent herpes outbreaks are commonly presaged by perceptible symptoms such as a burning, tingling or itching sensation, often accompanied by the formation of small bumps on the skin. When an infected subject detects these symptoms, administration of the composition of the invention can prevent the progression of the symptoms to ulcer formation. It is expected that prophylactic administration of the composition will prevent, or at least decrease the frequency and duration of ulcer formation resulting from lipid enveloped virus infections.

In particular, the above concentrations of lysine, butylated hydroxytoluene, and *Echinacea* make the nutritional supplement of the present invention suitable for use in the treatment of herpes type I and II and other lipid enveloped virus infections.

Additionally, the nutritional supplement may be combined with a carrier and/or excipient to produce a nutritional supplement composition. A wide number of acceptable carriers are known in the nutritional supplement arts, and the carrier can be any suitable carrier. The carrier need only be suitable for administration to animals, including humans, and be able to act as a carrier without substantially affecting the desired activity of the nutritional supplement. Also, the carrier(s) may be selected based upon the desired administration route and dosage form of the composition. For example, the nutritional supplement compositions according to the present invention are suitable for use in a variety of dosage forms, such as liquid form and solid form.

Further, a pharmaceutical composition may be prepared by combining L-lysine, butylated hydroxytoluene and *Echinacea* with a pharmaceutically acceptable carrier and/or excipient.

The composition of the invention can be present in association with one or more pharmaceutically acceptable carriers and/or excipients and/or diluents and/or adjuvants, and if desired other active ingredients.

Compositions intended for oral use can be prepared according to any method known to the art for the manufacture of pharmaceutical compositions and such compositions can contain one or more sweetening agents, flavoring agents, coloring agents, preservative agents, stabilizers, buffers, dispersants, thickeners, solubilizing agents, and the like, as well as vitamins, minerals, coenzymes, organic or inorganic antioxidants or precursors thereof, additional nutritional supplements and/or herbal extracts, and other active ingredients.

Illustrative examples of sweetening agents which may be used in the compositions of the present invention include, but are not limited to, fructose, sucrose, sugar, dextrose, lactose, maltose, maltodextrins, corn syrup solids, honey solids, mannitol, sorbitol, xylitol, saccharin, aspartame, cyclamates, acesulfame K, neohesperidin dihydrochalcone, other super sweeteners, and mixtures thereof, which may be added to the carrier in amounts sufficiently low so as not to chemically interact with the nutritional supplement.

Illustrative examples of flavoring agents which may be used in the compositions of the present invention include, but are not limited to, peppermint, peppermint-menthol, eucalyptol, wintergreen, licorice, clove, cinnamon, spearmint, cherry, lemon, orange, lime, menthol and various combinations thereof.

The compositions of the present invention can be formulated in a suitable manner for oral use, for example, as tablets, troches, lozenges, aqueous or oily suspensions, dispersible powders or granules, emulsions, hard or soft capsules, or syrups or elixirs.

Tablets contain the nutritional supplement in admixture with non-toxic pharmaceutically acceptable excipients that are suitable for the manufacture of tablets. These excipients can be for example, inert diluents, such as calcium carbonate, sodium carbonate, sodium citrate, lactose, calcium phosphate, sodium phosphate, microcrystalline cellulose, corn starch, potato starch, and cellulose esters such as cellulose acetate, ethyl cellulose; granulating and disintegrating agents, for example, corn starch, or alginic acid, or complex silicates; binding agents, for example starch, polyvinylpyrrolidone, PEG-8000, gelatin or gum acacia, and lubricating agents, for example magnesium stearate, stearic acid, sodium lauryl sulfate, or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the nutritional supplement is mixed with an inert solid diluent, for example, calcium carbonate, calcium phosphate or kaolin, or as soft gelatin capsules wherein the nutritional supplement is mixed with water or an oil medium, for example peanut oil, liquid paraffin or olive oil.

Aqueous suspensions contain the nutritional supplement in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the nutritional supplement in a vegetable oil, for example arachis oil, olive oil, sesame oil or coconut oil, or in a mineral oil such as liquid paraffin. The oily suspensions can contain a thickening agent, for example beeswax, hard paraffin or acetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the nutritional supplement in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oil phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, preservative, flavoring, and coloring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Ingestion of the nutritional supplement of the present invention, or compositions comprising the nutritional supplement and one or more carriers and/or excipients has also been surprisingly found to be beneficial in the treatment of patients with herpes simplex types I and II infections, other lipid enveloped virus infections and cold sores.

The effective amount of nutritional supplement that can be combined with the carrier and/or excipients to produce a single dosage form varies depending upon the host treated and the particular mode of administration. Dosage unit forms generally contain between from about 5 mg to about 5000 mg of the nutritional supplement. Doses of up to 1000-5000 mg are suitable for daily consumption.

In the treatment of cold sores the preferred dose is 1500 mg of the nutritional supplement, taken twice on the first day and to be taken daily over subsequent four day period.

Oral or parenteral administration of an effective amount of the nutritional supplement either alone or formulated as the compositions of the present invention relieves the symptoms of a person suffering from the abovementioned ailments.

EXAMPLE 1

A nutritional supplement was prepared containing 480 mg (64 wt. %) L-Lysine, 250 mg (33 wt. %) of butylated hydroxy toluene, and 20 mg (3 wt. %) of *Echinacea* as well as other inactive filler ingredients, providing a single dosage form containing a total 1500 mg of the active ingredients.

A 65 year old white male with known history of herpes labials (HSV-1) complained of itching and burning along his upper lip, having noticed the viral prodrome the prior night. The patient was given the nutritional supplement to take twice a day for 5 days. On physical exam after completing the five day course of therapy, the patient was noted to have a small (~2-3 mm) crusted lesion on his upper lip. The patient stated that the prodromal symptoms responded immediately to the nutritional supplement and that there was a very brief vesicular outbreak followed by immediate crusting. The patient stated that the duration of his outbreaks were usually 10-14 days and that this resolution was significantly faster.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

I claim:

1. A method of treating a patient infected with a herpes virus consisting essentially of:
administering to the patient an effective amount of a nutritional supplement consisting essentially of L-lysine, butylated hydroxytoluene and *Echinacea* and a pharmaceutically acceptable carrier; and
wherein the nutritional supplement is administered by one or more of oral and parenteral administration.

2. The method of claim 1, wherein the patient is administered from about 5 mg to about 5000 mg per day of the nutritional supplement.

3. The method of claim 2, wherein the patient is administered from about 1000 mg to about 5000 mg per day of the nutritional supplement.

4. The method of claim 3, wherein the patient is administered about 1500 mg per day of the nutritional supplement.

5. The method of claim 3, wherein the nutritional supplement consisting essentially of from about 40 to about 80 wt. % L-lysine, from about 20 to about 50 wt. % butylated hydroxytoluene and from about 1 to about 10 wt. % *Echinacea*.

6. The method of claim 5, wherein the nutritional supplement consisting essentially of about 64 wt. % L-lysine, about 33 wt. % butylated hydroxytoluene and about 3 wt. % *Echinacea*.

7. A method of preventing a nascent herpes outbreak from developing into a herpes ulcer, consisting essentially of the steps:
  identifying a nascent herpes outbreak; and
  administering about 1000 mg to about 5000 mg per day of a composition consisting essentially of from about 40 to about 80 wt. % L-lysine, from about 20 to about 50 wt. % butylated hydroxytoluene and from about 1 to about 10 wt. % *Echinacea* and a pharmaceutically acceptable carrier; and
  wherein the nutritional supplement is administered by one or more of oral and parenteral administration.

8. The method of claim 7, wherein the composition consisting essentially of from about 50 to about 70 wt. % L-lysine, from about 25 to about 40 wt. % butylated hydroxytoluene and from about 1 to about 10 wt. % *Echinacea*.

9. The method of claim 8, wherein the nutritional supplement consisting essentially of about 64 wt. % L-lysine, about 33 wt. % butylated hydroxytoluene and about 3 wt. % *Echinacea*.

* * * * *